(12) United States Patent
Pillai (10) Patent No.: US 9,511,214 B2
(45) Date of Patent: *Dec. 6, 2016

(54) METHODS OF TRANSVASCULAR RETROGRADE ACCESS PLACEMENT AND DEVICES FOR FACILITATING THEREIN

(75) Inventor: Lakshmikumar Pillai, Morgantown, WV (US)

(73) Assignee: VASCULAR ACCESS TECHNOLOGIES, INC., Morgantown, WV (US)

( * ) Notice: Subject to any disclaimer, the term of this patent is extended or adjusted under 35 U.S.C. 154(b) by 3006 days.

This patent is subject to a terminal disclaimer.

(21) Appl. No.: 11/424,131

(22) Filed: Jun. 14, 2006

(65) Prior Publication Data

US 2012/0136366 A1    May 31, 2012

Related U.S. Application Data

(63) Continuation of application No. 11/381,229, filed on May 2, 2006, now abandoned.

(51) Int. Cl.
*A61M 25/09* (2006.01)
*A61M 39/02* (2006.01)
(Continued)

(52) U.S. Cl.
CPC ......... *A61M 39/0247* (2013.01); *A61M 25/09* (2013.01); *A61M 25/09041* (2013.01);
(Continued)

(58) Field of Classification Search
CPC .............. A61M 39/0247; A61M 25/09; A61M 25/09041; A61M 25/0068; A61M 25/0133; A61M 25/0136; A61M 2025/09175; A61M 2025/0681; A61M 2025/09125; A61M 2025/09116; A61M 2025/0273; A61M 2025/0282; A61M 2025/0258
(Continued)

(56) References Cited

U.S. PATENT DOCUMENTS 4,559,039 A     12/1985  Ash et al.
4,790,825 A  *  12/1988  Bernstein et al. ....... 604/170.02
(Continued)

FOREIGN PATENT DOCUMENTS

WO    WO 2004/018029 A2    3/2004

OTHER PUBLICATIONS

WIPO Publication WO 2005/053547 to Cook Incorporated, Vascular Occlusion Methods, Systems and Devices, Jun. 16, 2005.*
(Continued)

*Primary Examiner* — Victor Nguyen
*Assistant Examiner* — Jonathan Hollm
(74) *Attorney, Agent, or Firm* — Shay Glenn LLP (57) ABSTRACT

The present invention relates to methods of transvascular retrograde access placement and to devices that facilitate these methods. For purposes of the present invention, transvascular retrograde access placement generally comprises the insertion of a vascular catheter into a central blood vessel through the puncturing of the central blood vessel from the inside of the central blood vessel with a needle or other similarly configured device, or a needle-tipped guidewire of the present invention, and exiting that needle from the patient through the skin rather than the traditional approach of inserting a needle from the outside of the skin surface to the inside of a blood vessel.

12 Claims, 13 Drawing Sheets

(51) Int. Cl.
*A61M 25/00* (2006.01)
*A61M 25/01* (2006.01)
*A61M 25/06* (2006.01)

(52) U.S. Cl.
CPC ..... *A61M 25/0068* (2013.01); *A61M 25/0133* (2013.01); *A61M 25/0136* (2013.01); *A61M 2025/0681* (2013.01); *A61M 2025/09116* (2013.01); *A61M 2025/09125* (2013.01); *A61M 2025/09175* (2013.01); *A61M 2039/0258* (2013.01); *A61M 2039/0273* (2013.01); *A61M 2039/0282* (2013.01)

(58) Field of Classification Search
USPC ........ 600/585, 114, 115, 424, 433; 606/108, 606/159, 167, 170, 185, 192, 194, 195; 604/43, 604/164.02–164.13, 115, 116, 506–510, 532
See application file for complete search history.

(56) References Cited

U.S. PATENT DOCUMENTS

| | | | |
|---|---|---|---|
| 4,966,163 | A | 10/1990 | Kraus et al. |
| 5,421,348 | A | 6/1995 | Larnard |
| 5,492,530 | A | 2/1996 | Fischell et al. |
| 5,685,820 | A | 11/1997 | Riek et al. |
| 5,733,248 | A * | 3/1998 | Adams et al. ............... 600/585 |
| 6,047,700 | A * | 4/2000 | Eggers et al. ............... 128/898 |
| 6,102,926 | A | 8/2000 | Tartaglia et al. |
| 6,217,527 | B1 | 4/2001 | Selmon et al. |
| 6,475,226 | B1 | 11/2002 | Belef et al. |
| 6,508,777 | B1 * | 1/2003 | Macoviak et al. ........... 604/4.01 |
| 6,554,794 | B1 | 4/2003 | Mueller et al. |
| 6,623,480 | B1 | 9/2003 | Kuo et al. |
| 6,726,677 | B1 | 4/2004 | Flaherty et al. |
| 6,955,657 | B1 | 10/2005 | Webler |
| 7,008,979 | B2 | 3/2006 | Schottman et al. |
| 7,374,567 | B2 | 5/2008 | Heuser |
| 7,648,517 | B2 | 1/2010 | Makower et al. |
| 8,019,420 | B2 | 9/2011 | Hine et al. |
| 2001/0012924 | A1 | 8/2001 | Milo et al. |
| 2001/0023346 | A1 | 9/2001 | Loeb |
| 2002/0004666 | A1 * | 1/2002 | Schwager et al. ........... 606/191 |
| 2002/0029060 | A1 | 3/2002 | Hogendijk et al. |
| 2002/0120250 | A1 | 8/2002 | Altman |
| 2002/0133168 | A1 | 9/2002 | Smedley et al. |
| 2002/0169377 | A1 | 11/2002 | Khairkhahan et al. |
| 2004/0039371 | A1 | 2/2004 | Tockman et al. |
| 2004/0059280 | A1 * | 3/2004 | Makower et al. ................ 604/8 |
| 2004/0082850 | A1 | 4/2004 | Bonner et al. |
| 2004/0133168 | A1 * | 7/2004 | Salcudean et al. ...... 604/164.13 |
| 2004/0181150 | A1 * | 9/2004 | Evans et al. .................. 600/433 |
| 2004/0181238 | A1 * | 9/2004 | Zarbatany et al. ........... 606/108 |
| 2005/0101984 | A1 | 5/2005 | Chanduszko et al. |
| 2005/0149097 | A1 | 7/2005 | Regnell et al. |
| 2005/0209579 | A1 | 9/2005 | Yacoubian et al. |
| 2006/0009737 | A1 | 1/2006 | Whiting et al. |
| 2006/0135962 | A1 | 6/2006 | Kick et al. |
| 2006/0247750 | A1 | 11/2006 | Seifert et al. |
| 2007/0021767 | A1 | 1/2007 | Breznock |
| 2007/0203515 | A1 | 8/2007 | Heuser et al. |
| 2008/0249565 | A1 | 10/2008 | Michler et al. |
| 2012/0136366 | A1 | 5/2012 | Pillai et al. |
| 2013/0172922 | A1 | 7/2013 | Pillai et al. |

OTHER PUBLICATIONS

Mark W. Mewissen, M.D., Revascularization of Long FP Arterial Occlusions, Endovascular Today, Mar. 2004, pp. 2-4.
Outback LTD Re-Entry Catheter, LuMend, Inc., Product Resources, http://www.lumend.com/images/Technology/Product/brochure.pdf.
Rosch-Uchida Transjugular Liver Access Set, Cook Group, Inc., Device Animations, http://www.cookmedical.com/di/educationMedia.do?mediaId=591.
Pillai, Lakshmikumar; U.S. Appl. No. 11/381,229 entitled "Methods of Transvascular Retrograde Access Placement and Devices for Facilitating Therein," filed May 2, 2006.
Pillai, Lakshmikumar; U.S. Appl. No. 12/366,517 entitled "Methods of Transvascular Retrograde Access Placement and Devices for Facilitating the Placement," filed Feb. 5, 2009.
Huang et al.; Journal of Applied Physiology; vol. 77; pp. 2907-2911; 1994.
Pillai, et al.; U.S. Appl. No. 12/861,716 entitled "Methods of Transvascular Retrograde Access Placement and Devices for Facilitating the Placement," filed Aug. 23, 2010.
O'Callaghan et al.; Dynamics of stab wounds: force required for penetration of various cadaveric human tissues; Forensic Sci. Int'l; vol. 104; pp. 173-178; 1999.
Pillai, Lakshmikumar; U.S. Appl. No. 13/904,876 entitled "Transvascular Access Methods," filed May 29, 2013.
Pillai et al.; U.S. Appl. No. 13/906,122 entitled "Tranvascular Access Device and Method," filed May 30, 2013.

* cited by examiner

METHODS OF TRANSVASCULAR RETROGRADE ACCESS PLACEMENT AND DEVICES FOR FACILITATING THEREIN

This application is a continuation of the co-pending U.S. patent application Ser. No. 11/381,229, filed May 2, 2006, the entire disclosure of which is hereby incorporated by this reference.

The present invention relates to methods of transvascular retrograde access placement and to devices that facilitate in the performance of these methods.

The following description of the present invention and certain embodiments thereof can be best understood when read in conjunction with the following drawings, where like structure is indicated with like reference numerals and in which.

Generally, the method of the present invention, referred to as "transvascular retrograde access placement" herein, comprises the puncturing of a central blood vessel from the inside of the vessel with a needle or other similarly configured device, and exiting that needle from a patient through the skin; therefrom, a vascular catheter may be inserted into said central blood vessel by means of said needle or other device. The methods of transvascular retrograde access placement of the present invention preferably are performed in a jugular 14 or subclavian 16 vein, although it is contemplated by the present invention that these methods may be performed through the puncture of any central blood vessel of a vascular system of a patient. As shown in FIGS. 9-12 and hereinafter described, preferred devices of the present invention include a guidewire 50 modified to comprise a needle-tip portion 52; and an angled-tip vascular catheter 40 modified to comprise (a) a channel 46 positioned exteriorly along a length of the vascular catheter 40, and/or (b) one or more diagnostically-opaque markers 44 positioned within or about the angled-tip 42 of the vascular catheter 40.

Figure 1:
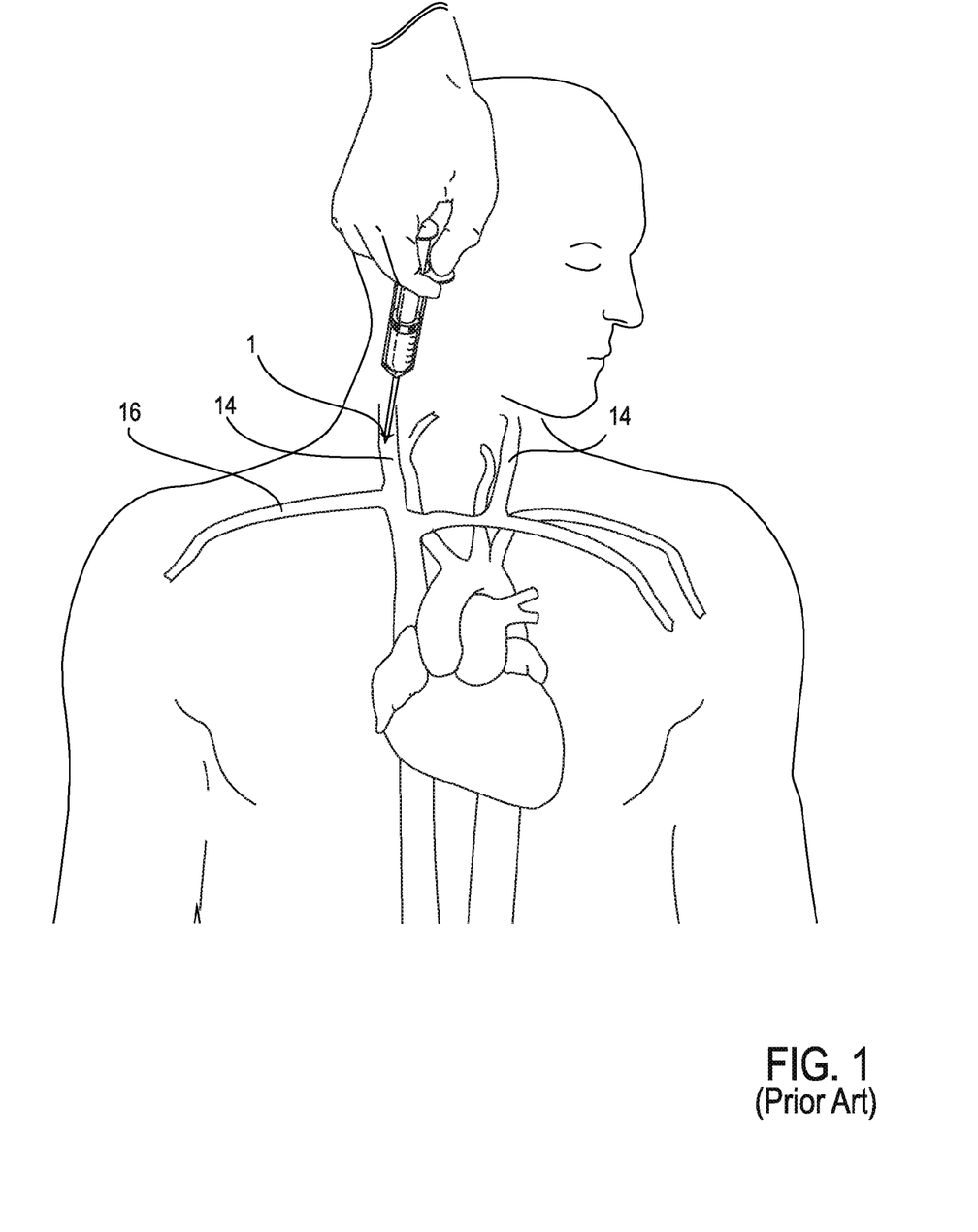
FIG. 1 is an illustration of a technique of the prior art of performing upper trunk central venous catheterization.

The methods of transvascular retrograde access placement of the present invention are presented as alternatives to traditional approaches for performing central venous catheterization, all of which generally involve the placing of catheters, needles 1, and/or wires into jugular 14 or subclavian 16 veins. In reference to the traditional approaches, the predominant technique utilizes central venous cannulation. This technique, shown in FIG. 1, involves inherent risks with potentially serious consequences and adverse effects to the patient due to the technique's blind puncture of the percutaneous tissue (from the outside of the skin to the inside of the central vein) at the site of the vein location. More specifically, this technique comprises, with or without fluoroscopic guidance, the percutaneous puncture of either the jugular 14 or subclavian 16 vein with a hollow needle 1, and the passage of a guidewire into the punctured vein through the needle 1. Thereafter, the guidewire assists with the insertion of, and is ultimately replaced by, a vascular catheter. The percutaneous puncture site generally is determined by anatomic landmarks ("dead reckoning") or, less commonly, with the aid of transcutaneous ultrasound.

While this traditional technique is usually accomplished with few, if any, complications and minimal pain to the patient, the technique, due to the blind percutaneous puncture, inherently carries significant risks. These risks include potentially disabling or life-threatening injuries such as, but not limited to, injury to adjacent vascular and lymphatic structures, nerves, and/or pneumothorax/hemothorax, especially when the traditional technique is performed on children or adult patients with challenging anatomy or conditions, like morbid obesity. The methods of transvascular retrograde access placement of the present invention greatly reduce these risks by eliminating the blind percutaneous puncture. To further reduce risks, advanced diagnostic imaging technologies may be used with the method of the present invention to visualize the internal puncture of the central blood vessel of a patient.

More specifically, the method of transvascular retrograde access placement of the present invention generally comprises performing cannulation of a primary blood vessel, such as, but not limited to, a femoral 12 or antecubital 18 vein; inserting an angled-tip vascular catheter 40 into the blood vessel; positioning the angled-tip vascular catheter 40, which may or may not be modified according to the present invention, inside a central blood vessel, preferably, but not necessarily, a jugular 14 or subclavian 16 vein, of the vascular system; passing a needle or other similarly configured device, or a guidewire 50 modified according to a device of the present invention to comprise a needle-tip portion 52, through or about the vascular catheter 40; and puncturing an inner wall 15 of that central blood vessel with the needle, passing the needle through the subcutaneous tissue, and exiting the needle through the patient's skin. The vascular catheter 40 may now be removed from the patient. A secondary vascular catheter 60 may then be passed over the needle from the outside of the skin such that an end of the secondary vascular catheter 60 is placed within the punctured central blood vessel while a second end of the secondary vascular catheter 60 is exposed from the skin of the patient. The needle is then fully removed from the patient at either the exit site or the cannulation site.

According to the herein described methods of the present invention for performing transvascular retrograde access placement, these methods may generally further comprise using advance diagnostic imaging technologies (such as, but not limited to, fluorscopy). By providing a diagnostically-opaque substance, usually an iodinated vascular contrast material, to the vascular system of the patient so that the vascular system is visible through advanced diagnostic imaging technologies, the level of safety is enhanced in performing these methods. This diagnostically-opaque substance generally is introduced into the vascular system prior to the insertion of the vascular catheter 40 into the primary blood vessel and, again, in the vicinity of a central blood vessel immediately prior to the puncture of a wall 15 of the central blood vessel.

The primary blood vessel cannulation may be achieved by means of the Modified Seldinger Technique, wherein the desired vessel or cavity is punctured with a sharp hollow needle; a round-tipped guidewire is then advanced through the lumen of the needle, and the needle is withdrawn. An introducer is then inserted over the guidewire, and into the vessel; a "sheath" or blunt cannula is passed through the introducer; and the guidewire and introducer are withdrawn. The sheath can then be used to introduce catheters into the vessel.

Figure 2:
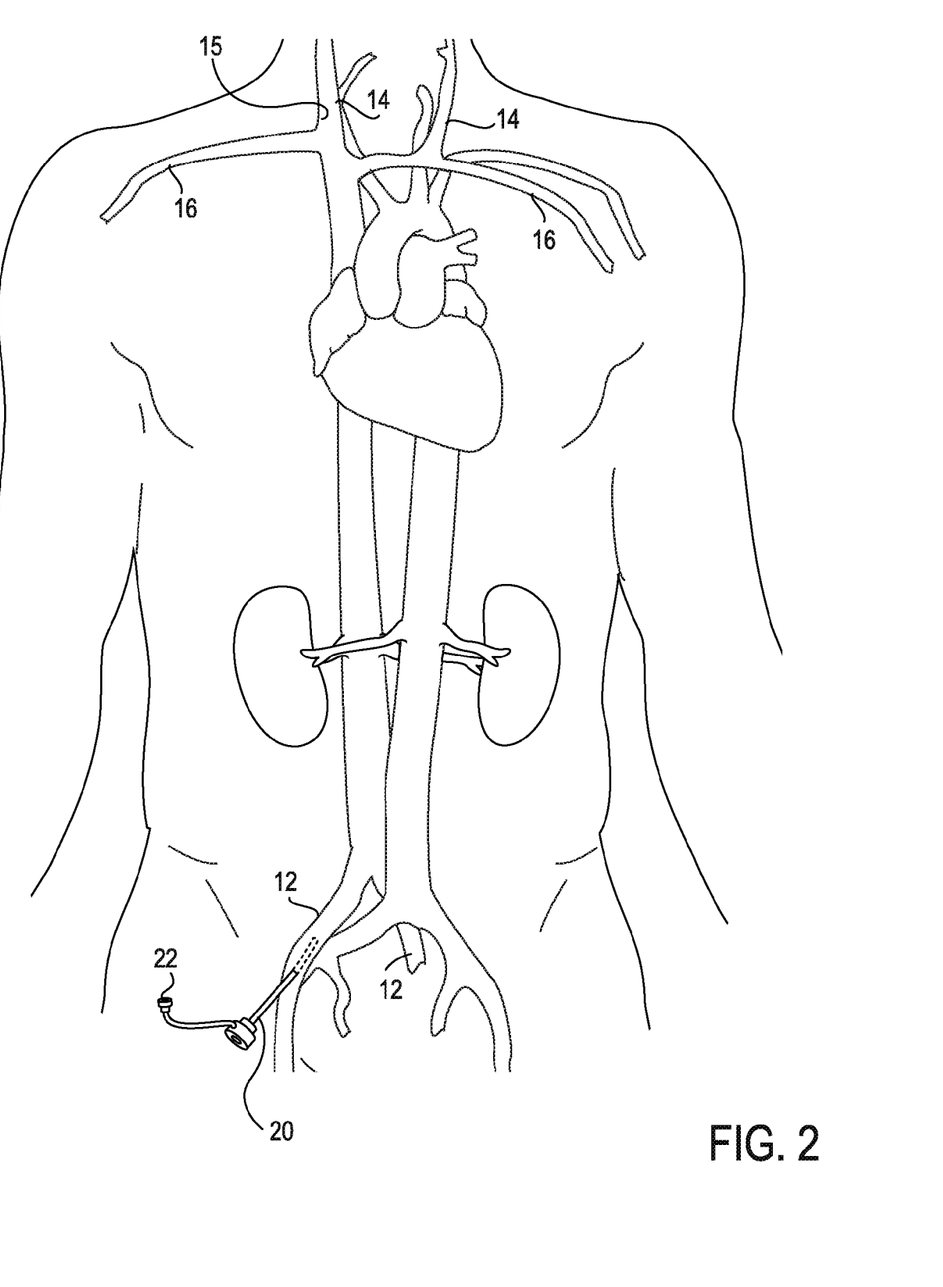
FIG. 2 is an illustration of a vascular sheath inserted into a femoral vein of the central venous system of a patient.

In accordance with the methods of the present invention, the Modified Seldinger Technique typically, but not necessarily, is achieved with an 18-gauge hollow needle, measuring about 2 and ⅞ inches in length, and a 5 cc syringe secured to the end of the 18-gauge needle opposite of the needle-tip. Typically, a femoral vein 12 is percutaneously cannulated with the needle. Once blood from the femoral vein 12 is aspirated into the syringe, the syringe is removed while the needle is held in place. Through this needle, a short guidewire, such as, but not limited to, a J-tip wire measuring about 0.035 inches in diameter and about 20 centimeters in length, may be advanced up the femoral vein 12 and into the iliac vein. The needle is then removed while the short guidewire is held in place. Thereafter, as shown in FIG. 2, a vascular sheath 20, generally measuring about 10 centimeters in length and typically, but not necessarily, comprising a removable stiff introducer and a hemostatic valve 22, is advanced over the short guidewire and into the femoral vein 12. The vascular sheath 20 preferably is a 5 French (F) sheath, but may be a 6 F or a 4 F sheath, or other similarly sized and configured sheath. (French/3.14=inner diameter of sheath or catheter in millimeters).

Then, with the vascular sheath 20 being substantially introduced into the patient, the short guidewire and the stiff introducer are removed and the vascular sheath 20 may be flushed, generally by inserting heparinized saline solution into the vascular sheath 20 through the hemostatic valve 22. It is contemplated by the methods of the present invention that the Modified Seldinger Technique may be performed with other similarly sized and configured needles, syringes, sheaths, and/or wires.

Figure 3:
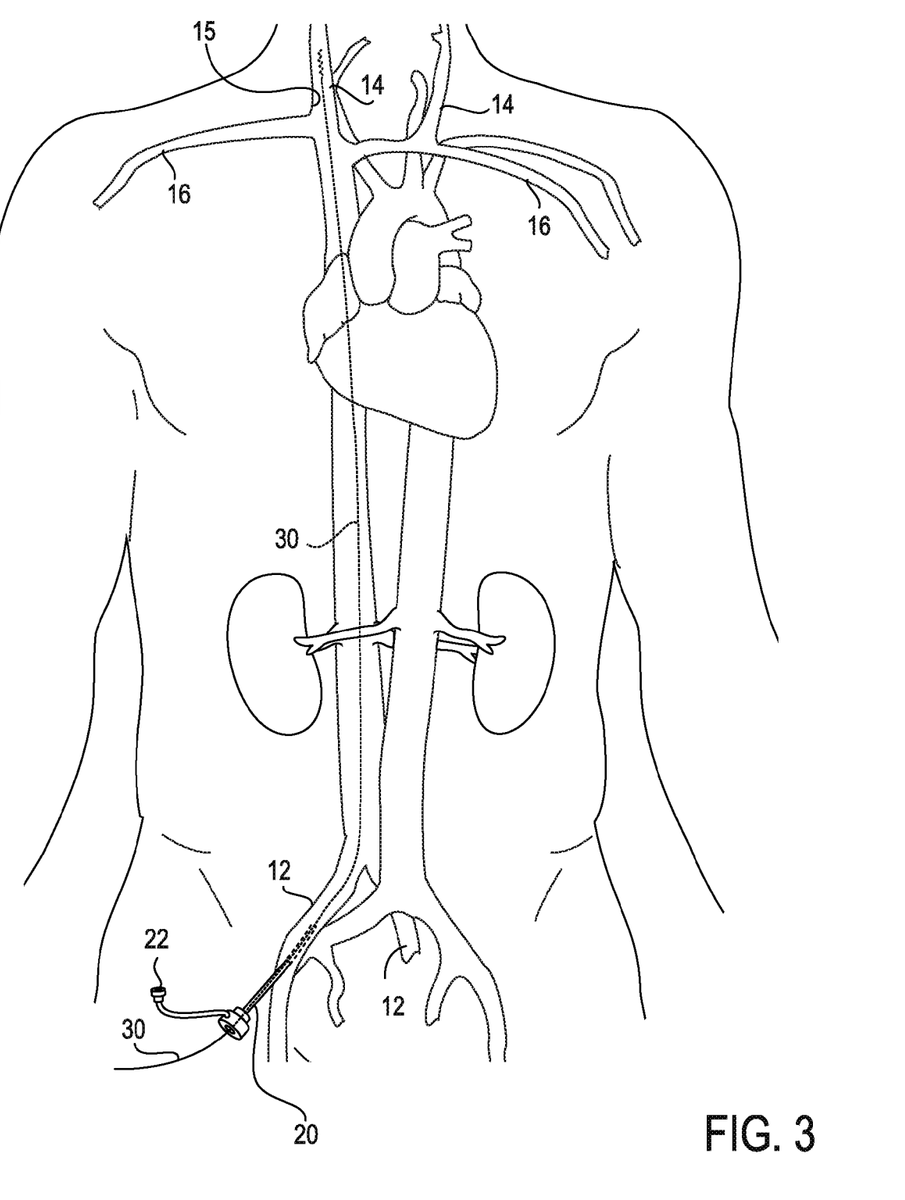
FIG. 3 is an illustration of a general use guidewire passed through a femoral venous vascular sheath and the venae cavae to a jugular vein.
Figure 4:
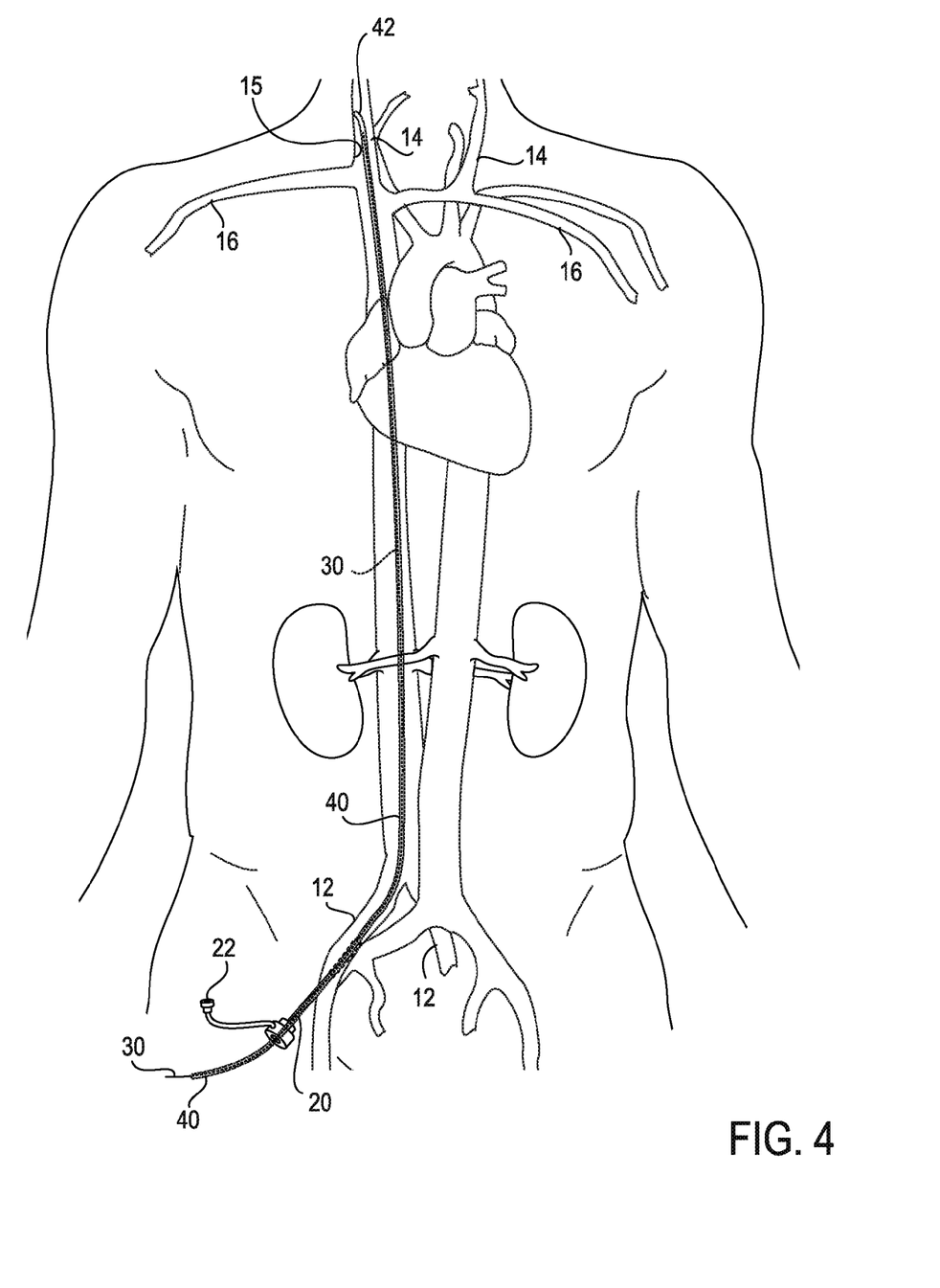
FIG. 4 is an illustration of an angled-tip vascular catheter passed over a general use guidewire and to a jugular vein.

Thereafter, as depicted in FIG. 3, a general use guidewire 30, typically, but not necessarily, measuring 0.035 inches in diameter, may be passed through the vascular sheath 20 and may be positioned in the vicinity of a jugular vein 14. Following the insertion and positioning of the general use guidewire 30, the angled-tip vascular catheter 40 may be passed over the general use guidewire 30, as shown in FIG. 4, after which the general use guidewire 30 is removed. For purposes of all of the herein described methods of the present invention, the angled-tip vascular catheter 40 preferably is a 5 F catheter, but may be a 4 F catheter, or other similarly sized and configured catheter. This vascular catheter 40 generally measures about 100 centimeters in length and comprises an angled-tip 42, which generally, but not necessarily, is angled at 45 degrees from the axis of the vascular catheter 40 and is about 1.5 centimeters in length. The vascular catheter 40 may further comprise a lubricious coating on the inside or outside, or both, areas of the vascular catheter 40.

Figure 5:
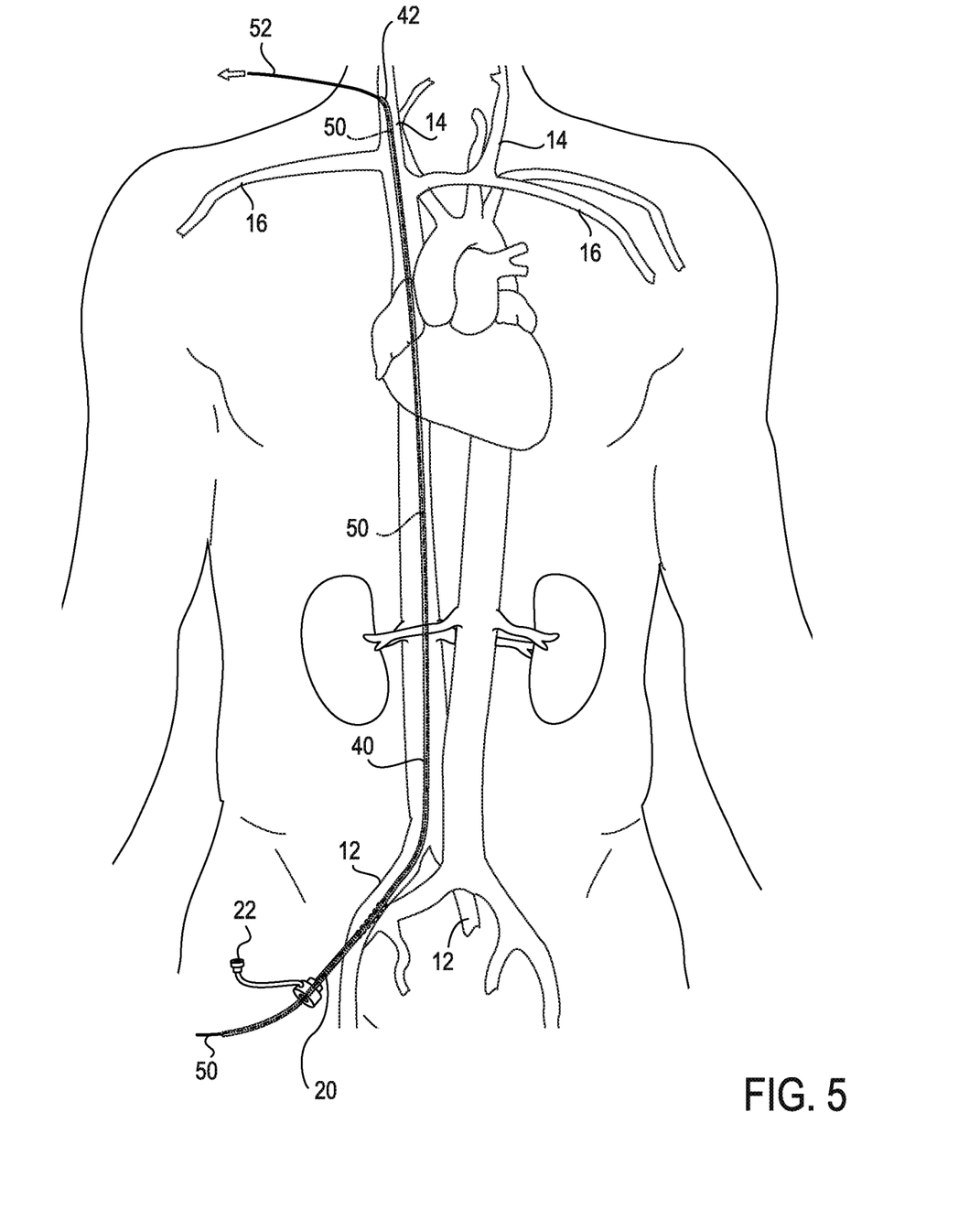
FIG. 5 is an illustration of an embodiment of a needle-tipped guidewire of the present invention inserted, via the femoral venous vascular sheath, through the angled-tip vascular catheter and used to puncture an inner wall of the jugular vein.

The vascular catheter 40, shown in FIG. 4, may then be positioned in the jugular vein 14 with the angled-tip 42 facing an inner wall 15 of the jugular vein 14. As depicted in FIG. 5, once the vascular catheter 40 is properly positioned, preferably under continuing diagnostic imaging, a needle or other similarly configured device, but, preferably, a needle-tip portion 52 of a modified stiff intravascular guidewire 50, may be passed through the end of the angled-tip 42 of the vascular catheter 40 and be used to puncture the inner wall 15 of the jugular vein 14. This stiff guidewire 50 is modified according to the device of the present invention to comprise this needle-tip portion 52 as hereinafter described.

Figure 6:
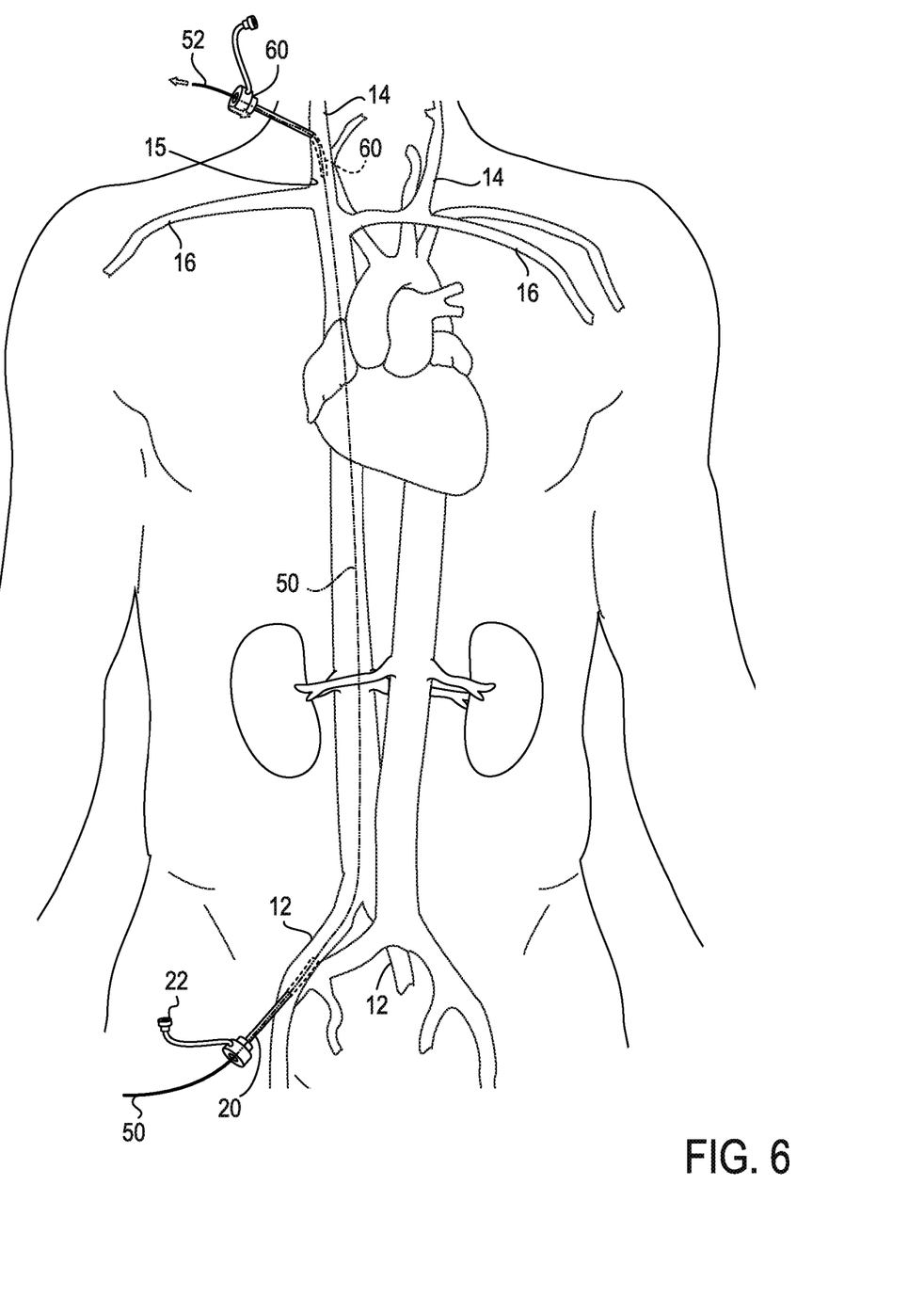
FIG. 6 is an illustration of a secondary vascular catheter passed over the needle-tipped guidewire outside the mid-neck skin surface and an end of the secondary vascular catheter inserted into the jugular vein.
Figure 7:
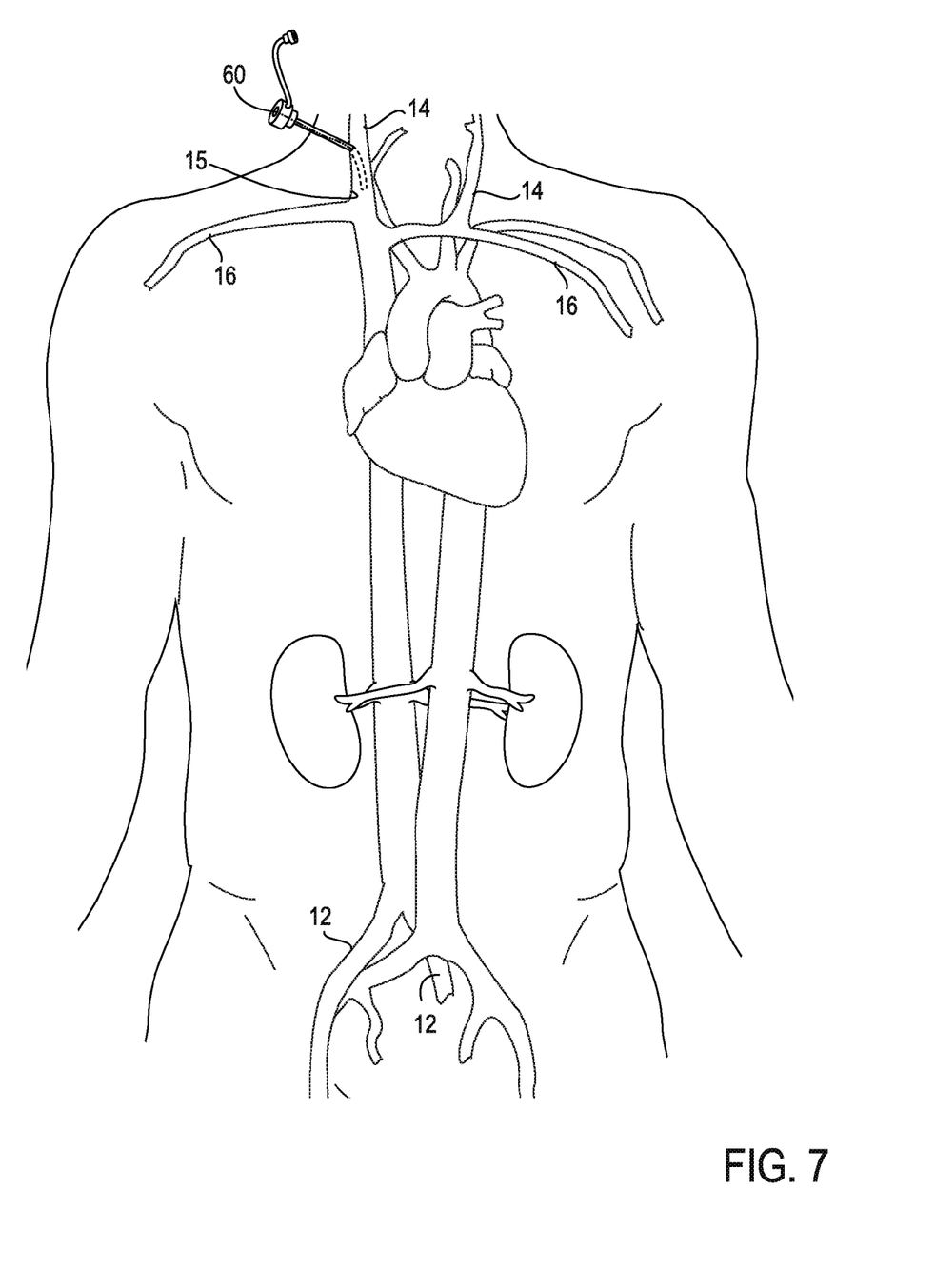
FIG. 7 is an illustration of an end of the secondary vascular catheter placed in the jugular vein after the needle-tipped guidewire and femoral vascular sheath have been removed from the venous system of the patient.

Thereafter, the needle, or the needle-tip portion 52 and a length of the needle-tipped guidewire 50, generally are passed through the subcutaneous tissue and exited through the skin of the patient (typically at mid-neck area when the central blood vessel punctured is a jugular vein 14), where they are recovered and pulled above the surface of the skin, as shown in FIG. 5. The vascular catheter 40 may then be removed from the vascular system of the patient, leaving the needle-tipped guidewire 50 in position. As shown in FIG. 6, a secondary vascular catheter 60 may then be passed over the needle or needle-tip portion 52 and the length of the needle-tipped guidewire 50 such that one end of the secondary vascular catheter 60 is placed within the jugular vein 14 while a second end is exposed from the skin of the patient. Thereafter, as shown in FIG. 7, the femoral vascular sheath 20 and the needle-tipped guidewire 50 of the present invention are removed from the patient while the secondary vascular catheter 60 remains in place. Pressure is then applied over the femoral venapuncture site for several minutes.

In accordance with yet another method of the present invention, a method of transvascular retrograde access placement varies generally from the previously described methods in that this method typically utilizes an angled-tip vascular catheter 40 modified as described hereinafter to comprise a channel 46 that is positioned exteriorly along a length of the vascular catheter 40. This channel 46 generally is configured in a diameter of at least about that of a 22-gauge needle and is positioned such that it is runs along substantially the entire length of the vascular catheter 40. In this method, after the vascular catheter 40 comprising the exterior channel 46 passes over the general use guidewire 30 and is positioned in the jugular vein 14, or other central blood vessel, the general use guidewire 30 is removed from the vascular catheter 40 and may be, but is not necessarily, replaced with a curved-tip stiff, solid obturator 70 comprising a relatively fixed curved-tip 72, at, for example, 45 degrees from the axis of the obturator.

Figure 12:
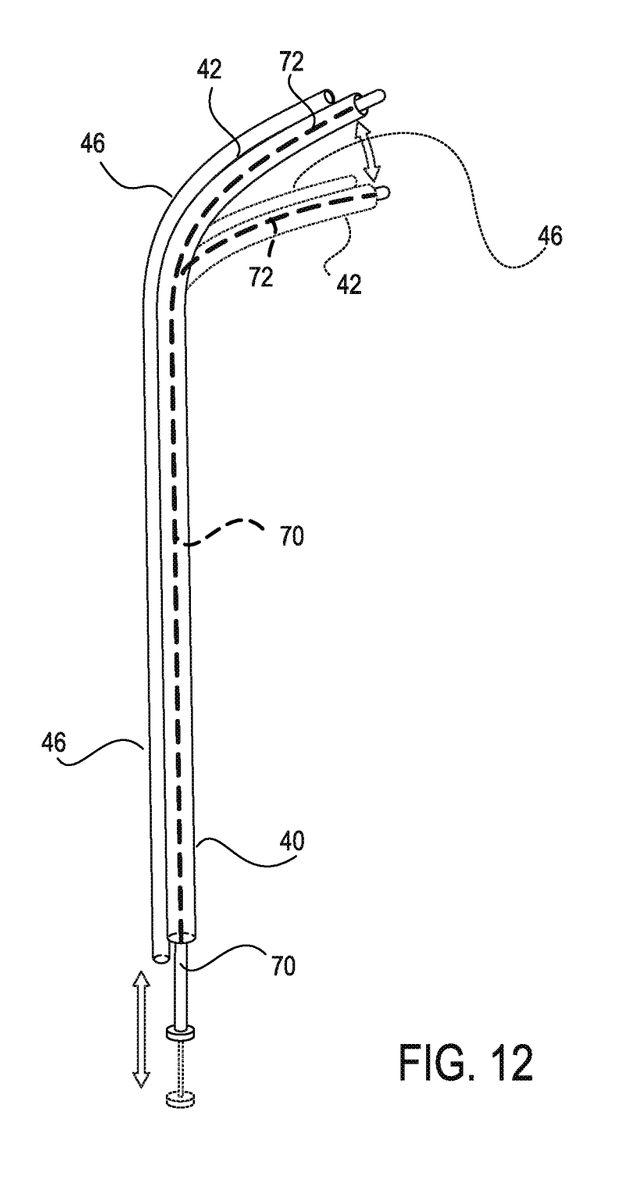
FIG. 12 is an illustration showing the adjustability of the degree of angle of an angled-tip of a vascular catheter of the present invention adjusted by advancing or withdrawing the curved-tip stiff obturator.

The vascular catheter 40, as mentioned above, comprises an angled-tip 42, with a predefined angle (for example, 45 degrees from the axis of the catheter). This angled tip 42, preferably being configured of materials comprising degrees of flexibility, may bend, thereby further varying the angle thereof from the central axis of the catheter 40 (between, for example 45 and 90 degrees), by means of and dependent on the length of insertion of the curved-tip 72 of the obturator 70 into the catheter 40 and the tip 42 thereof, as shown in FIG. 12. For example, assuming a 45 degree angled tip 42 and a 45 degree curved tip 72, when the obturator 70 is fully inserted into the vascular catheter 40 such that the curved-tip 72 is exposed from the end of the angled-tip 42, the curved-tip 72 corresponds with the angled-tip 42, thereby maintaining the 45 degree angle of the angled-tip 42. However, when the obturator 70 is partially inserted into or withdrawn from the angled-tip 42, the greater the degree of the angle of the angled-tip 42 becomes, up to, in this example, a 90 degree angle. This embodiment aids in the transvascular retrograde access placement method by enabling the surgeon to puncture through the inner wall 15 of jugular vein 14, or other central blood vessel, at a particular angle ranging, in this example, from 45 to 90 degrees.

Once the modified vascular catheter 40/curved-tip obturator 70 assembly is properly positioned in the jugular vein 14, a needle or a stiff intravascular guidewire 50, described herein as modified according to the present invention to comprise a needle-tip portion 52, may be inserted into the exterior channel 46 of the modified vascular catheter 40. The angled-tip 42 of the catheter 40 is then oriented to face the inner wall 15 of the jugular vein 14. The needle-tip portion 52 of the needle-tipped guidewire 50 may then pass through the tip of the exterior channel 46 of the modified vascular catheter 40 and puncture the inner wall 15 of the jugular vein 14. Thereafter, the needle-tip portion 52 and a length of the needle-tipped guidewire 50 may be passed up through the subcutaneous tissue, and exited through the skin, and the procedure continues as hereinbefore described.

It is contemplated by the present invention that all of the herein described methods of transvascular retrograde access placement procedure may be performed in any central blood vessel of the vascular system other than the preferred jugular vein 14, wherein the needle, the needle-tipped guidewire 50, or any other similar device, may exit the patient through another area of the patient. For example, the transvascular retrograde access placement procedure may be performed in a subclavian vein 16, wherein a needle, a needle-tipped guidewire 50, or other similar device exits the patient through skin of the upper trunk just below a clavicle.

Figure 8:
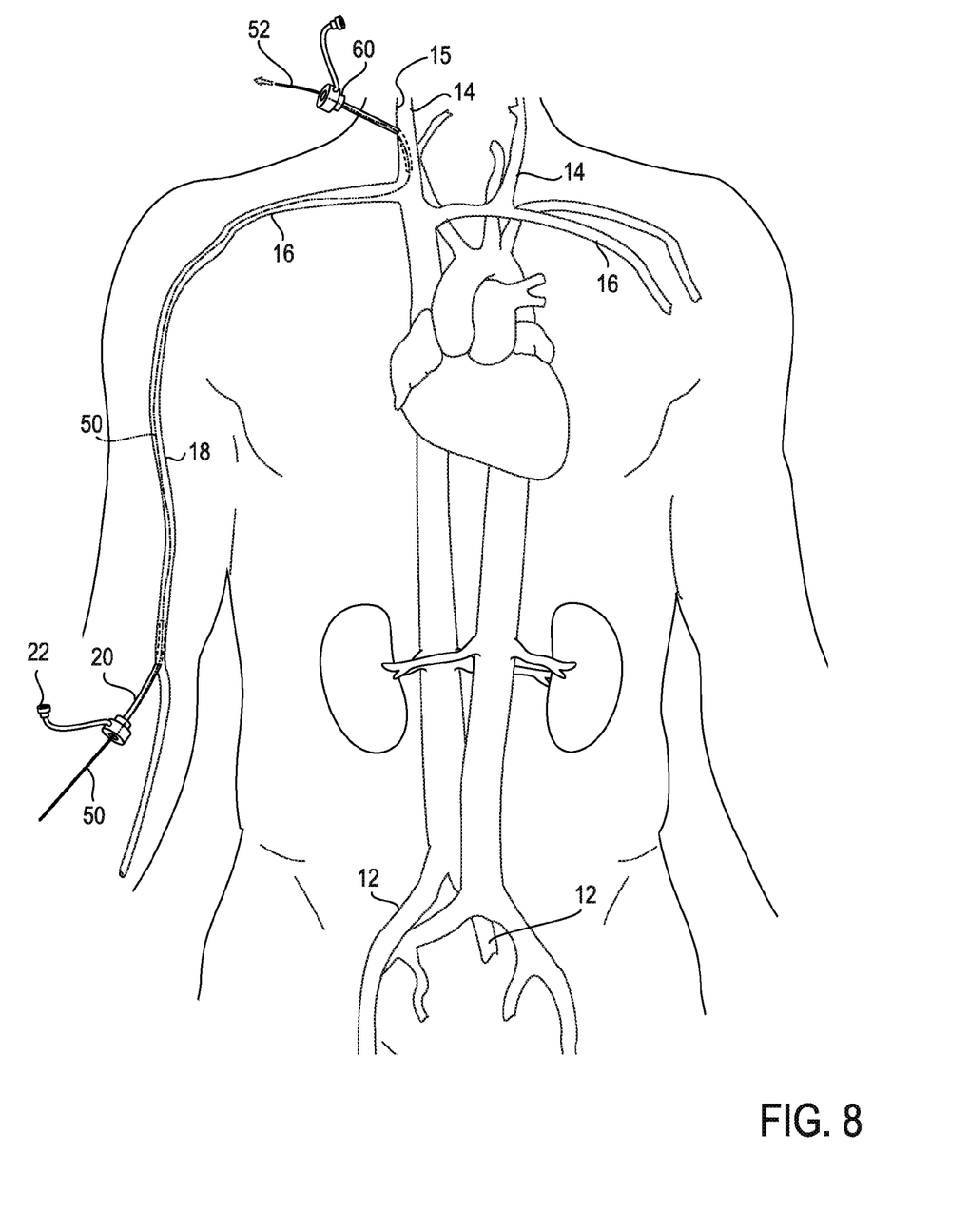
FIG. 8 is an illustration of an embodiment of transvascular retrograde access placement of the present invention introduced through an antecubital vein.
Figure 9:
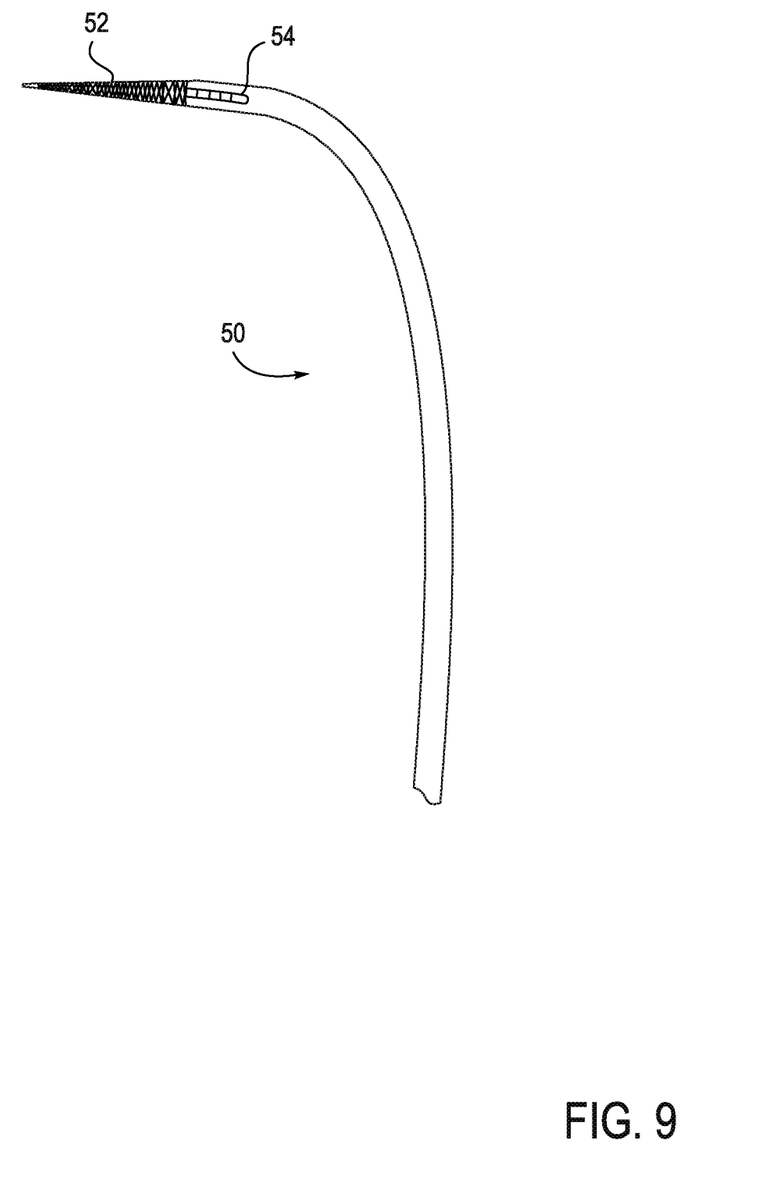
FIG. 9 is an illustration of an embodiment of a needle-tipped guidewire of the present invention.

In accordance with yet another method of the present invention, a method of transvascular retrograde access placement varies generally from the previously described methods in that, rather than the femoral vein cannulation described above, this method comprises an antecubital blood vessel cannulation. An antecubital blood vessel is located in the antecubital fossa of a patient's arm. As shown in FIG. 8, this method more specifically comprises, through the application of the Modified Seldinger Technique and the insertion of a vascular sheath 20, inserting into what is preferably, but not necessarily, an antecubital vein 18, a general use guidewire 30, over which is passed a vascular catheter 40, which may or may not be modified according to embodiments of the devices of the present invention. The vascular catheter 40 is then passed up the vascular system to a jugular 14 or subclavian 16 vein, or other central vein. Thereafter, the remainder of this embodiment generally proceeds in accordance with the previously described embodiments of the present invention.

The present invention also relates to devices that facilitate the herein described methods of transvascular retrograde access placement. As mentioned above, one such device, shown in FIG. 9, is a stiff intravascular guidewire 50 that is modified to comprise a needle-tip portion 52 at one end thereof, typically measuring at least about 1 centimeter in length. The needle-tipped guidewire 50 may further comprise a lubricious coating on its exterior surface. The needle-tipped guidewire 50 may also or alternatively be configured such that the needle-tip portion 52 may be removable from the remainder of the guidewire 50, for example, but not by way of limitation, by means of a screw/thread mechanism 54 similar to that utilized with the Amplatzer vascular plug occluder detachment system. Furthermore, this needle-tipped guidewire 50 preferably measures a length of at least about 260 centimeters, but it is contemplated by the present invention that a length measuring from about 150 to about 300 centimeters may be utilized to perform the herein described methods of the present invention, and may be configured in a variety of diameters, such as, but not limited to, 0.035 inches, 0.018 inches, or 0.014 inches, so that it may be utilized in a variety of catheterization procedures involving blood vessels other than central blood vessels.

Due to the unique configuration of this guidewire 50 comprising the needle-tip portion 52, the guidewire 50 provides a simpler configuration and easier operation than that offered by existing surgical needle, or needle/guidewire assembly, embodiments available in the prior art. Thus, a surgeon performing a herein described method of transvascular retrograde access placement may use a single component, the needle-tipped guidewire 50, to insert into a vascular catheter 40, puncture a wall 15 of a central blood vessel, and pass through the skin of the patient, rather than just a needle with a needle-tip, over which a secondary vascular catheter to be inserted into the punctured central blood vessel might not pass, or a needle/guidewire assembly that requires two components be inserted into the vascular catheter 40 and the vascular system, thereby being more costly and cumbersome.

Figure 10A:
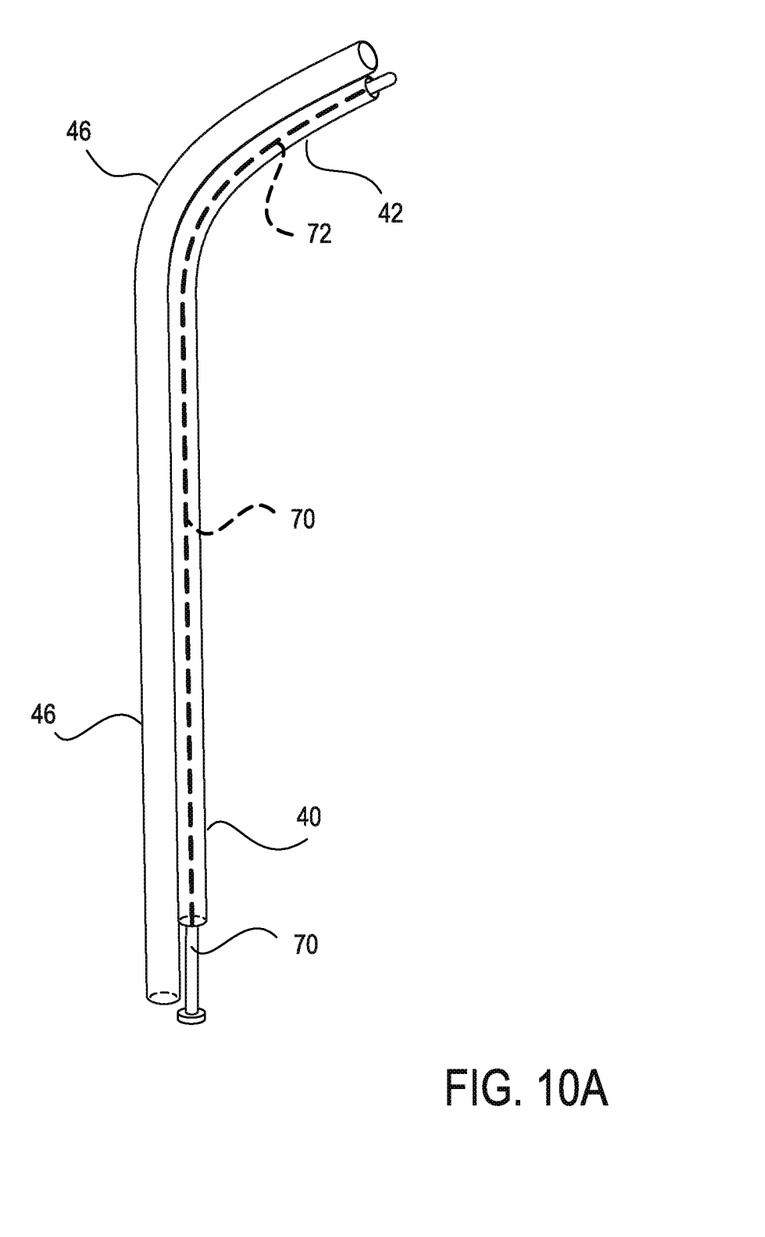
FIG. 10A is an illustration of an embodiment of an angled-tip vascular catheter of the present invention having a curved-tip stiff obturator passed through it and a channel positioned exteriorly along a length of the vascular catheter.
Figure 10B:
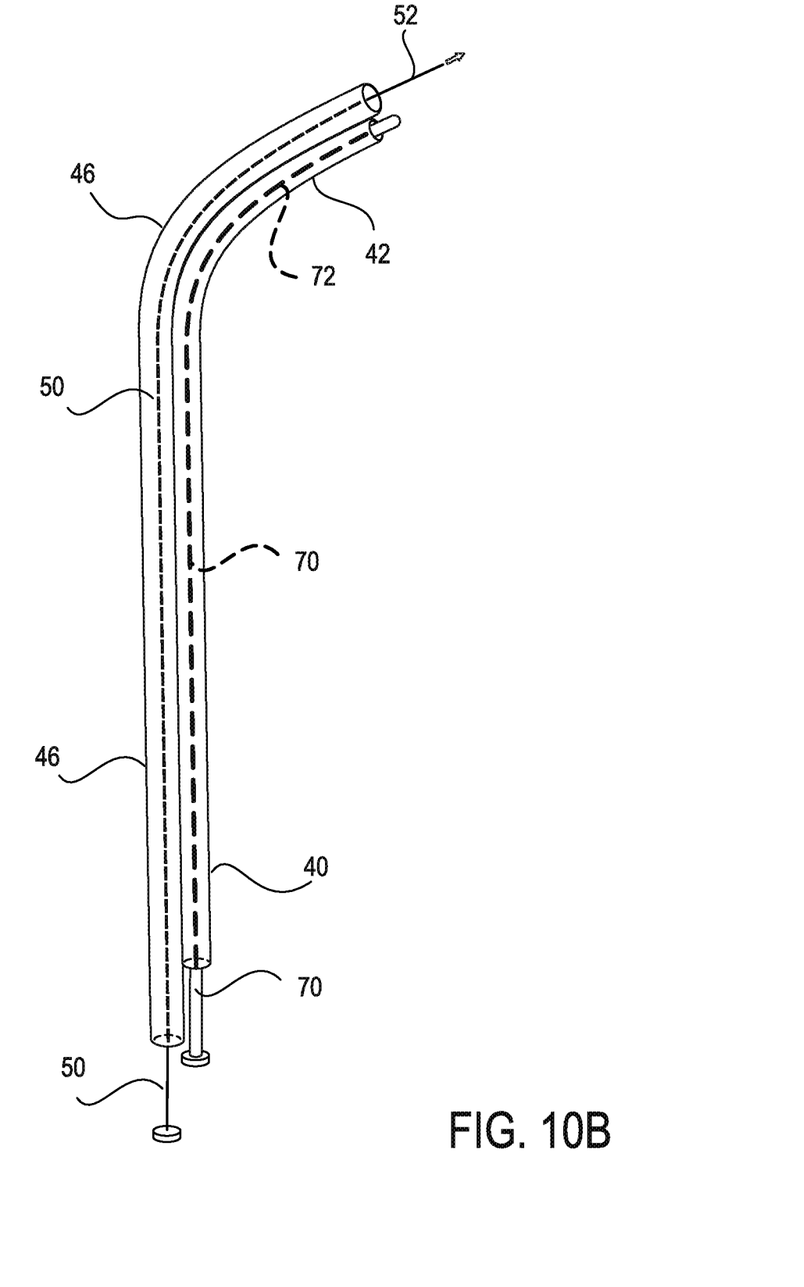
FIG. 10B is an illustration of an embodiment of an angled-tip vascular catheter with an exterior channel of the present invention having a curved-tip stiff obturator passed through the vascular catheter and a needle-tipped guidewire of the present invention passed through the exterior channel.

Another embodiment of devices that facilitate the herein described methods relates to the modification of a vascular catheter 40, as described hereinabove, to comprise a channel 46 positioned exteriorly along a length of the vascular catheter 40, as shown in FIG. 10A. This exterior channel 46 generally is configured in a diameter of at least about that of a 22-gauge needle and is positioned such that it runs along substantially the entire length of the vascular catheter 40. As shown in FIG. 10B, the exterior channel 46 serves as a guide for the insertion of a needle, or other similarly configured device, or a needle-tipped guidewire 50 of the present invention, that may be used to puncture a central blood vessel. It is contemplated by the present invention that this modified vascular catheter 40 and the exterior channel 46 may be provided in different configurations to ease its application to various other blood vessels.

Figure 11A:
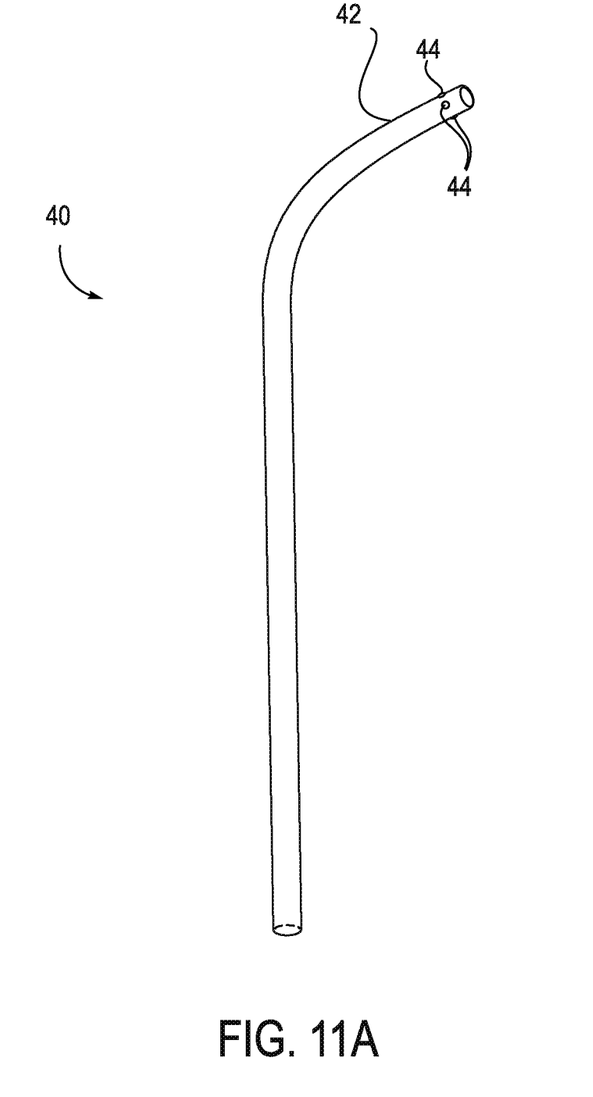
FIG. 11A is an illustration of an embodiment of an angled-tip vascular catheter of the present invention comprising diagnostically-opaque markers positioned about the angled-tip.
Figure 11B:
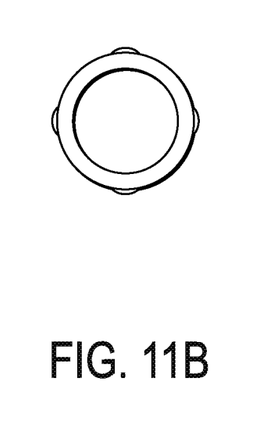
FIG. 11B is a frontal view of an angled-tip and diagnostically-opaque markers positioned about the angled-tip of an embodiment of a vascular catheter of the present invention.

Another or enhanced embodiment of devices that facilitate the herein described methods relates to the modification of an angled-tip vascular catheter 40 to comprise one or more diagnostically-opaque markers 44 that may be positioned within or about the angled-tip 42 of the vascular catheter 40, as shown in FIGS. 11A and 11B. In a preferred embodiment, a vascular catheter 40 is configured with four gold markers 44 positioned about the exterior of the angled-tip 42. The diagnostically-opaque markers 44 may be configured to indicate, through advanced diagnostic imaging technologies, the orientation of the angled-tip 42 of the vascular catheter 40 in relation to an inner wall 15 of a central blood vessel. In another or enhanced embodiment, the angled-tip 42 of the vascular catheter 40 may be provided with diagnostically-opaque markers 44 dispersed within the material forming the angled-tip 42. This indication aids in the procedure by enabling a surgeon to monitor the orientation of the angled-tip 42 of the vascular catheter 40, through which a needle, or other similar device, or needle-tip portion 52 of a needle-tipped guidewire 50 of a device of the present invention, may be exposed, and to ensure the proper alignment of the angled-tip 42 with the inner wall 15 of the central blood vessel prior to the puncturing of the inner wall 15.

For purposes of the methods and devices of the present invention described herein, the term "diagnostically-opaque" means that the substance introduced to the vascular system to enable visualization and the markers 44 provided to the angled-tip 42 of the vascular catheter 40 may be diagnostically recognized through advanced diagnostic imaging technologies, such as, but not limited to, high-resolution ultrasound, X-ray, CAT-scan, fluoroscopy, and/or magnetic resonance imaging (MRI).

It is noted that terms like "preferably," "commonly," "generally," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "device" is utilized herein to represent a combination of components and individual components, regardless of whether the components are combined with other components.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method of performing transvascular retrograde access placement in a central blood vessel of a patient, the central blood vessel selected from a group consisting of a jugular vein or a subclavian vein, said method comprising:
    inserting a vascular catheter into a femoral vein or an antecubital vein and positioning said vascular catheter within said central blood vessel such that a portion of said vascular catheter faces a desired exit site on a wall of said central blood vessel, the vascular catheter comprising an angled-tip;
    passing a needle from said vascular catheter through said desired exit site on said wall of said central blood vessel and skin of said patient; and
    passing an end of a secondary vascular catheter through said exit site and into said central blood vessel.

2. The method of claim 1, further comprising providing a diagnostically-opaque substance into a vascular system of said patient prior to the positioning step.

3. The method of claim 1, wherein said needle is supported by a guidewire.

4. The method of claim 1, further comprising introducing said needle through a channel exterior to said vascular catheter.

5. The method of claim 4, further comprising advancing an angled-tip stiff obturator through said vascular catheter.

6. The method of claim 5, wherein a distal tip of said angled-tip stiff obturator comprises an angle with respect to a proximal length of said obturator, and wherein advancing said obturator through said vascular catheter comprises advancing said obturator to a distal end of the catheter; and altering an angle of the distal end of the catheter in accordance with said angle of said angled tip.

7. The method of claim 1, prior to the passing said needle through the exit site, further comprising advancing said needle through said vascular catheter to said desired exit site.

8. The method of claim 7, wherein advancing said needle through said vascular catheter to the desired exit site comprises advancing a needle-tipped guidewire through a channel exterior to said vascular catheter.

9. The method of claim 1, prior to passing said needle through said exit site, further comprising forming an opening at said desired exit site in said wall of said central blood vessel with said needle.

10. The method of claim 1, wherein passing an end of the secondary vascular catheter through said exit site comprises passing said secondary vascular catheter over the needle.

11. The method of claim 1, after passing said needle through said exit site, further comprising pulling said vascular catheter and said needle through said skin; and removing said vascular catheter from said patient while leaving said needle in position.

12. The method of claim 1, further comprising visualizing diagnostically-opaque markers on said vascular catheter prior to passing the needle through said desired exit site.

* * * * *